United States Patent
Luo et al.

(10) Patent No.: US 11,776,694 B2
(45) Date of Patent: Oct. 3, 2023

(54) METHOD AND SYSTEM FOR IDENTIFYING POTENTIAL CONTAMINANTS IN TEST PLATES

(71) Applicant: Helix OpCo, LLC, San Mateo, CA (US)

(72) Inventors: Shishi Luo, San Francisco, CA (US); William Lee, Mountain View, CA (US); Ruomu Jiang, Palo Alto, CA (US); Magnus Isaksson, Santa Clara, CA (US)

(73) Assignee: Helix, Inc., San Mateo, CA (US)

( * ) Notice: Subject to any disclaimer, the term of this patent is extended or adjusted under 35 U.S.C. 154(b) by 0 days.

(21) Appl. No.: 17/542,664

(22) Filed: Dec. 6, 2021

(65) Prior Publication Data

US 2023/0178236 A1    Jun. 8, 2023

(51) Int. Cl.
| | | |
|---|---|---|
| *G16H 50/20* | (2018.01) | |
| *G16H 70/60* | (2018.01) | |
| *G16H 30/40* | (2018.01) | |
| *G16B 40/10* | (2019.01) | |
| *G06F 18/2415* | (2023.01) | |
| *C12Q 1/686* | (2018.01) | |

(52) U.S. Cl.
CPC ......... *G16H 50/20* (2018.01); *G06F 18/2415* (2023.01); *G16B 40/10* (2019.02); *G16H 30/40* (2018.01); *G16H 70/60* (2018.01); *C12Q 1/686* (2013.01)

(58) Field of Classification Search
None
See application file for complete search history.

(56) References Cited

FOREIGN PATENT DOCUMENTS

JP    6936674 B2 *  9/2021  .......... C12Q 1/6837

OTHER PUBLICATIONS

Cheng et al. (Sensors (Basel). Oct. 2016; 16(10): 1600, pp. 1-10) (Year: 2016).*
Kohler et al. (Molecular Cancer 2009, 8:105, pp. 1-8) (Year: 2009).*
Ahmed et al. (Science of The Total Environment, vol. 805, Jan. 20, 2022, 149877, pp. 1-20) (Year: 2022).*
Goldstein (The Annals of Statistics, 1982, vol. 10, No. 1, pp. 174-183) (Year: 1982).*
Williams et al. (Journal of Applied Microbiology, 2012, 114, 152-160) (Year: 2012).*
Anzenbacher et al. (Chem. Soc. Rev., 2010, 39, 3954-3979) (Year: 2010).*
Can You Tell Random and Non-Random Apart? https://toward data science.com; Nov. 2, 2021.

* cited by examiner

*Primary Examiner* — Pablo S Whaley
(74) *Attorney, Agent, or Firm* — Duft & Bornsen, PC

(57) ABSTRACT

Systems and methods are provided for quality control for biological testing. One embodiment is a system that includes a liquid handler that applies samples of genetic material to a test plate comprising an array of wells, a Polymerase Chain Reaction (PCR) device that amplifies the genetic material, and an analysis device that determines, based on a change in visual appearance of each well, a numerical value indicating whether a corresponding sample is representative of a disease state. The system also includes a quality assurance server that identifies a pattern of the numerical values, and determines a likelihood of the pattern. In an event that the likelihood is less than a threshold value, the quality assurance server flags the test plate as potentially contaminated, and in an event that the likelihood exceeds the threshold value, the quality assurance server refrains from flagging the test plate as potentially contaminated.

20 Claims, 13 Drawing Sheets

FIG. 5

| 1 | 0 | 7 | 0 | 0 | 0 | 0 | 0 |
|---|---|---|---|---|---|---|---|
| 0 | 0 | 1 | 0 | 0 | 0 | 0 | 0 |
| 9 | 0 | 0 | 3 | 0 | 1 | 5 | 0 |
| 0 | 0 | 0 | 0 | 0 | 0 | 2 | 0 |
| 0 | 0 | 6 | 1 | 0 | 0 | 0 | 0 |
| 0 | 0 | 1 | 0 | 7 | 0 | 2 | 0 |
| 0 | 0 | 0 | 1 | 0 | 0 | 0 | 0 |
| 0 | 0 | 0 | 0 | 0 | 0 | 0 | 0 |
| 0 | 0 | 0 | 2 ←502 | 0 | 0 | 0 | 0 |
| 0 | 0 | 0 | 0 | 7 | 5 | 9 | 1 |
| 0 | 2 | 5 | 7 | 6 | 7 | 0 | 0 |
| 0 | 7 | 0 | 0 | 2 | 0 | 0 | 5 |
| 0 | 0 | 0 | 2 | 0 | 0 | 0 | 0 |
| 0 | 6 | 0 | 0 | 8 | 0 | 0 | 0 |
| 1 | 1 ←502 | 0 | 0 | 0 | 0 | 0 | 0 |

NUMERICAL VALUES 500

FIG. 6

| 0 | 0 | 0 | 0 | 0 | 0 | 0 | 0 |
|---|---|---|---|---|---|---|---|
| 0 | 6 | 0 | 0 | 8 | 0 | 0 | 0 |
| 0 | 0 | 0 | 0 | 0 | 0 | 0 | 0 |
| 0 | 7 | 0 | 0 | 0 | 0 | 0 | 5 |
| 0 | 0 | 5 | 7 | 6 | 7 | 0 | 0 |
| 0 | 0 | 0 | 7 | 5 | 9 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 7 | 0 | 0 | 0 | 0 |
| 0 | 6 | 0 | 0 | 0 | 0 | 0 | 0 |
| 0 | 0 | 0 | 0 | 0 | 0 | 0 | 0 |
| 9 | 0 | 0 | 0 | 0 | 0 | 5 | 0 |
| 0 | 0 | 0 | 0 | 0 | 0 | 0 | 0 |
| 0 | 0 | 7 | 0 | 0 | 0 | 0 | 0 |

NUMERICAL VALUES 500

FIG. 7

| | | | | | | | |
|---|---|---|---|---|---|---|---|
| 0 | 0 | 1 | 0 | 0 | 0 | 0 | 0 |
| 0 | 0 | 0 | 0 | 0 | 0 | 0 | 0 |
| 1 | 0 | 0 | 0 | 0 | 0 | 1 | 0 |
| 0 | 1 | 0 | 0 | 0 | 0 | 0 | 0 |
| 0 | 0 | 1 | 0 | 0 | 0 | 0 | 0 |
| 0 | 0 | 0 | 1 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 1 | 1 | 1 | 0 | 0 |
| 0 | 0 | 1 | 1 | 1 | 1 | 0 | 0 |
| 0 | 1 | 0 | 0 | 0 | 0 | 0 | 1 |
| 0 | 0 | 0 | 0 | 0 | 0 | 0 | 0 |
| 0 | 1 | 0 | 0 | 1 | 0 | 0 | 0 |
| 0 | 0 | 0 | 0 | 0 | 0 | 0 | 0 |

HIT TABLE 700

METHOD AND SYSTEM FOR IDENTIFYING POTENTIAL CONTAMINANTS IN TEST PLATES

FIELD

The disclosure relates to the field of biological analysis, and in particular, to reviewing samples that have undergone biological testing.

BACKGROUND

Biological testing is performed in order to detect the presence of conditions within individuals that may require treatment. Biological testing is particularly useful for detecting the presence of specific diseases. For example, biological testing may be used to determine whether segments of genetic material associated with a specific disease are present within a sample from an individual.

High-throughput testing comprises biological testing performed for a large number of samples (e.g., thousands of samples) over a short period of time (e.g., minutes or hours), at a rate that is impossible by hand. Efficient, accurate high-throughput testing is foundational to ensuring that the medical community has the capability to identify and respond to outbreaks of disease in a timely manner. For example, high-throughput testing has helped to limit the spread of coronavirus disease 2019 (COVID-19).

While high-throughput testing is critical for detecting and mounting a response to an outbreak, it remains vulnerable to contamination that reduces accuracy. For example, if a plate containing hundreds of samples has been contaminated by a liquid spill, then the accuracy of the high-throughput testing process may be compromised. Compounding this issue, it is particularly difficult to detect the presence of contamination, as many forms of contamination are invisible to the naked eye.

Hence, those who perform high-throughput testing of biological material within a laboratory environment continue to seek out enhanced systems and methods for achieving these goals.

SUMMARY

Embodiments described herein provide systems and methods that quantify the likelihood of patterns of positive (and/or inconclusive) test results within a plate of samples that have undergone biological testing. This technique does not require physical detection of contaminants, but rather determines, based on the geometric clustering of diagnostic results at a plate, whether the likelihood of those results is statistically improbable.

The systems and methods described herein provide a technical benefit over prior techniques, because they are objective in nature and hence not subject to human biases, are rigorously statistical in nature, are consistently repeatable, and are capable of being tuned to the rates of positivity found at specific test plates. That is, the techniques described herein are accurate, are capable of being performed efficiently and repeatedly without human intervention, and are capable of being tuned to the testing environment that they are implemented in.

One embodiment is a system that includes a liquid handler that applies samples of genetic material to a test plate comprising an array of wells, a Polymerase Chain Reaction (PCR) device that amplifies the genetic material at the array of wells, and an analysis device that, for each of the wells, determines, based on a change in visual appearance of the well caused by amplification of the genetic material at the well, a numerical value indicating whether a corresponding sample is representative of a disease state. The system also includes a quality assurance server that identifies a pattern of the numerical values at the array of wells of the test plate, and determines a likelihood of the pattern assuming a random distribution of the numerical values. In an event that the likelihood is less than a threshold value, the quality assurance server flags the test plate as potentially contaminated, and in an event that the likelihood exceeds the threshold value, the quality assurance server refrains from flagging the test plate as potentially contaminated, thereby permitting reporting of a diagnostic result.

A further embodiment is a method that includes applying samples of genetic material to a test plate comprising an array of wells, performing Polymerase Chain Reaction (PCR) to amplify the genetic material at the array of wells, for each of the wells: determining, based on a change in visual appearance of the well caused by amplification of the genetic material at the well, a numerical value indicating whether a corresponding sample is representative of a disease state. The method also includes identifying a pattern of the numerical values at the array of wells of the test plate, determining a likelihood of the pattern assuming a random distribution of the numerical values. The method further includes, in an event that the likelihood is less than a threshold value, flagging the test plate as potentially contaminated, and in an event that the likelihood exceeds the threshold value, refraining from flagging the test plate as potentially contaminated, thereby permitting reporting of a diagnostic result.

A further embodiment is a non-transitory computer readable medium embodying programmed instructions which, when executed by a processor, are operable for performing a method. The method includes applying samples of genetic material to a test plate comprising an array of wells, performing Polymerase Chain Reaction (PCR) to amplify the genetic material at the array of wells, for each of the wells: determining, based on a change in visual appearance of the well caused by amplification of the genetic material at the well, a numerical value indicating whether a corresponding sample is representative of a disease state. The method also includes identifying a pattern of the numerical values at the array of wells of the test plate, determining a likelihood of the pattern assuming a random distribution of the numerical values. The method further includes, in an event that the likelihood is less than a threshold value, flagging the test plate as potentially contaminated, and in an event that the likelihood exceeds the threshold value, refraining from flagging the test plate as potentially contaminated, thereby permitting reporting of a diagnostic result.

Other illustrative embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

FIG. 5 depicts numerical values assigned to wells that have been analyzed in an illustrative embodiment.

FIG. 6 depicts a filtered version of the numerical values of FIG. 5 in an illustrative embodiment.

FIG. 7 depicts the numerical values of FIG. 6 converted to hits and misses in an illustrative embodiment.

FIG. 9 depicts the motifs of FIG. 8 being matched against a pattern of hits in an illustrative embodiment.

DESCRIPTION

The figures and the following description depict specific illustrative embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
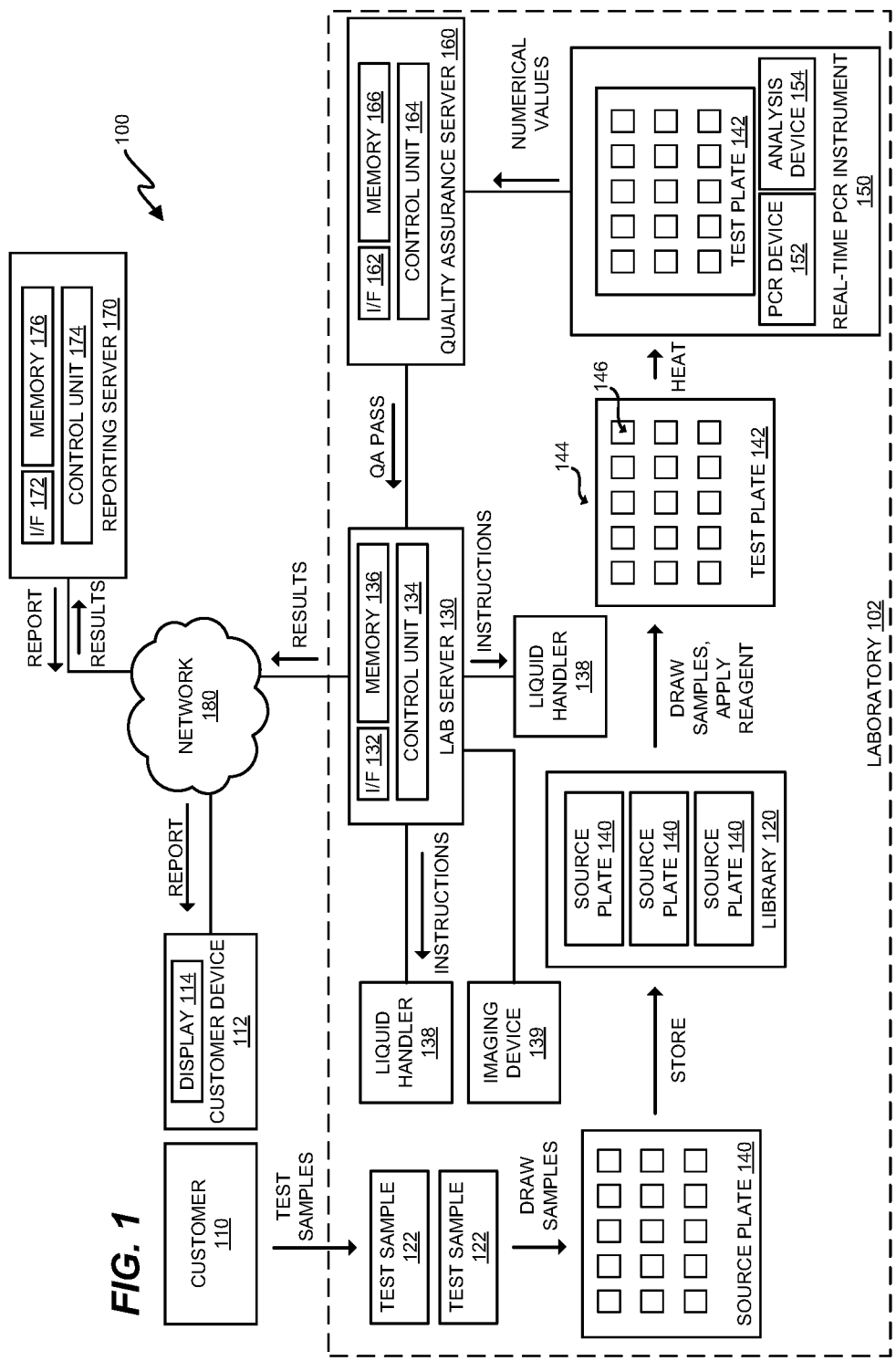
FIG. 1 is a block diagram depicting a high-throughput testing system that performs analysis and reporting in an illustrative embodiment.

FIG. 1 is a block diagram depicting a high-throughput testing system 100 that performs biological testing and reporting in an illustrative embodiment. High-throughput testing system 100 comprises any combination of systems, components, and/or devices that are capable of performing biological testing of samples at high throughput. As used herein, high throughput refers to rates of testing which are faster than could be performed by hand (e.g., via manual pipetting) in a laboratory. For example, high-throughput operations may perform pipetting at a rate of several hundred liquid transfer operations per minute, or more.

In this embodiment, laboratory 102 receives test samples 122 from a customer 110, such as a health care provider, for analysis. A test sample is a sample of biological material suitable for testing in order to detect the presence of a disease state or other biological condition. As used herein, a disease state is a condition of experiencing a specific disease that is diagnosable via testing, such as COVID-19. In one embodiment, test samples 122 comprise a suspension of genetic material corresponding to a specific person, organ, and/or portion of tissue, etc. The test samples 122 may be received from the customer 110 within distinct sealed tubes or other containers, in order to reduce the risk of cross-contamination. The number of test samples 122 received from the customer 110 at a point in time may comprise hundreds, thousands, or even tens of thousands.

The container for each test sample 122 may be labeled with a barcode, Quick Response (QR) code, or other identifying information. In this embodiment, the identifying information indicates a source of the test sample 122 (e.g., a patient name, a patient identifier (ID), a specific organ of a patient, a specific portion of tissue of a patient, etc.), a date that the test sample 122 was acquired, and/or desired biological tests to be performed upon the test sample 122. This information may be retrieved by operating an imaging system 139 (e.g., a camera, laser, or Radio Frequency Identifier (RFID) scanner), and then stored in a memory 136 of a lab server 130 for later linking to diagnostic results.

In this embodiment, lab server 130 comprises an interface (I/F) 132 for receiving communications from coupled devices, a control unit 134, and the memory 136, which stores instructions for utilization by the control unit 134. The interfaces 132 discussed herein may comprise Small Computer System Interface (SCSI), Serial Attached SCSI (SAS), Ethernet, wireless adapters, etc. configured to exchange information with coupled devices. The control units discussed herein may be implemented, for example, as custom circuitry, as a hardware processor executing programmed instructions, or some combination thereof. The memories discussed herein may comprise flash memory, one or more Hard Disk Drives (HDDs), optical storage devices, etc.

The lab server 130 controls and coordinates the actions of various devices within the laboratory 102. For example, the control unit 134 of the lab server 130 may generate instructions for a liquid handler 138 to retrieve test samples 122 from their containers and apply the test samples 122 to different wells at one or more source plates 140.

Liquid handler 138 comprises an automated tool capable of sampling, mixing, and/or combining test samples 122 in a liquid phase for the purposes of biological testing. For example, liquid handler 138 may comprise an automated electronic pipette, array of electronic pipettes, or other components that are capable of rapidly transferring predetermined amounts of liquid to new locations. A liquid handler 138 may transfer liquid for a large number of samples at a much higher rate (e.g., hundreds of times faster) than would be possible by hand. As each test sample 122 is applied to a different well of a source plate 140, the control unit 134 of the lab server 130 updates information in memory 136 to indicate the location of that test sample 122 on the source plate 140. After each test sample 122 has been applied to a unique well of the source plate 140, the source plate 140 is stored in library 120.

Library 120 maintains the test samples 122 at a temperature where the test samples 122 remain biologically stable and do not degrade. For example, the library 120 may comprise a refrigerator or other cooling device having multiple racks for receiving source plates 140, and may maintain the test samples 122 at a temperature between thirty-three and forty degrees Fahrenheit (° F.).

As test samples 122 are accumulated at source plates 140 within the library 120, the control unit 134 of the lab server 130 selects batches of the test samples 122 (e.g., from one or more customers 110) for testing at a test plate 142. A batch comprises a number of chosen test samples 122 up to the number of wells 146 at the test plate 142. To prepare for testing of the batch, lab server 130 provides instructions to a liquid handler 138 to transfer the test samples 122 of the batch from one or more source plates 140 of the library 120 to an array 144 of wells 146 of the test plate 142. The liquid handler 138 that transfers the test samples 122 from the source plates 140 to the test plate 142 may be the same liquid handler 138 discussed above, or another liquid handler 138.

As used herein, the array 144 comprises the wells 146 of test plate 142 which actually receive test samples 122. Thus, in some instances the array 144 comprises all wells 146 of the test plate 142, while in other instances where the test plate 142 is not filled with test samples 122, the array 144 comprises a subset thereof.

Each test sample 122 is transferred to a different well 146 of the test plate 142. Thus, after the test plate 142 has received the batch of test samples 122, each test sample 122 is located at a unique one of the wells 146. As used herein, transferring a test sample 122 from a well of a source plate 140 to a well 146 of a test plate 142 may comprise transferring some, but not all, of the test sample 122 residing at the source plate 140. This enables test samples 122 at a source plate 140 to be tested repeatedly if desired. After the test samples 122 have been applied to the wells 146 of the test plate 142, the control unit 134 updates information in memory 136 to associate each well 146 of the test plate 142 with identifying information for a corresponding test sample 122.

In this embodiment, before or after the test samples 122 have been added to the test plate 142, control unit 134 instructs a liquid handler 138 to apply a reagent to each of the wells 146 of the test plate 142. The reagent selectively reacts with portions of biological material (e.g., genetic material) that correspond with the disease state being tested for, causing corresponding wells 146 at the test plate 142 to exhibit a visual change. Thus, the reagent may vary depending on the disease state being tested for.

As used herein, biological material corresponds with a disease state if it is created or accumulated by the progression of that disease state. For example, genetic material corresponds with a disease state for coronavirus disease (COVID) when the genetic material is part of the genome of a coronavirus that causes the disease state.

In one embodiment, the reagent comprises a fluorescent reporter molecule that is utilized during a real-time Polymerase Chain Reaction (PCR) process. For example, the reagent may comprise a deoxyribonucleic acid (DNA)-specific or ribonucleic acid (RNA)-specific dye in the form of an oligonucleotide bound to a fluorescent die molecule.

Having received the test samples 122 and the reagent, the test plate 142 proceeds to a PCR device 152 (e.g., a thermocycler) and is heated to facilitate amplification of genetic material. In further embodiments where the biological material undergoing testing is not genetic material, use of a PCR device 152 may be omitted. An analysis device 154 (e.g., a fluorescent plate reader, light sensor, spectrometer that detects a specific wavelength of light, etc.) proceeds to visually quantify each of the wells 146, resulting in numerical values. In this embodiment, the analysis device 154 quantifies a fluorescence intensity of each of the wells 146 after PCR has been performed for a predetermined amount of time. However, in further embodiments and depending on the nature of the reagent, the analysis device 154 may quantify a color, opacity, absorbance, other visual characteristic, or other characteristic of any kind, for each of the wells 146. In this embodiment, the PCR device 152 and analysis device 154 are both integrated into a real-time PCR instrument 150 (e.g., a QUANTSTUDIO brand real-time PCR system).

The numerical values for each well 146 of the test plate 142 are transmitted to interface 162 of a quality assurance server 160. In this embodiment, the numerical values are numerical fluorescence intensities, measured as fluorophore units, and are each accompanied by information identifying a location (e.g., row and column) of a corresponding well 146 at the test plate 142. A control unit 164 reviews the numerical values based on instructions in memory 166, and determines whether the numerical values are indicative of contamination of the test plate 142, as will be discussed in detail with regard to FIG. 3 below.

In this embodiment, the numerical values do not suggest that the test plate 142 has been contaminated. Thus, the quality assurance server 160 transmits a message to the lab server 130 indicating a Quality Assurance (QA) pass. The lab server 130 then reports diagnostic results based on the numerical values to a reporting server 170 via a network 180 (e.g., the Internet, a private network, etc.). For example, the lab server 130 or quality assurance server 160 may associate distinct ranges of numerical values with a specific diagnosis (e.g., negative for a low range, inconclusive for a middle range, positive for a high range), and then assign a diagnosis to each test sample 122 in the batch based on the numerical value for a corresponding well 146.

At the reporting server 170, interface 172 compiles the received diagnostic results, and control unit 174 formats the results into a report in accordance with instructions in memory 176. The interface 172 then transmits the report via the network 180 (or another network) for handling by a customer device 112. The customer device 112 may comprise, for example, a computer, mobile device, cellular phone, etc. The customer device 112 presents the report (or data therein) via a display 114, such as a screen, in order to provide a diagnostic result to the customer 110. Within the report, each diagnostic result may be coupled with an identifier for the test sample 122, such as a specific patient name, a patient ID, or anonymized or de-identified versions thereof.

Figure 2:
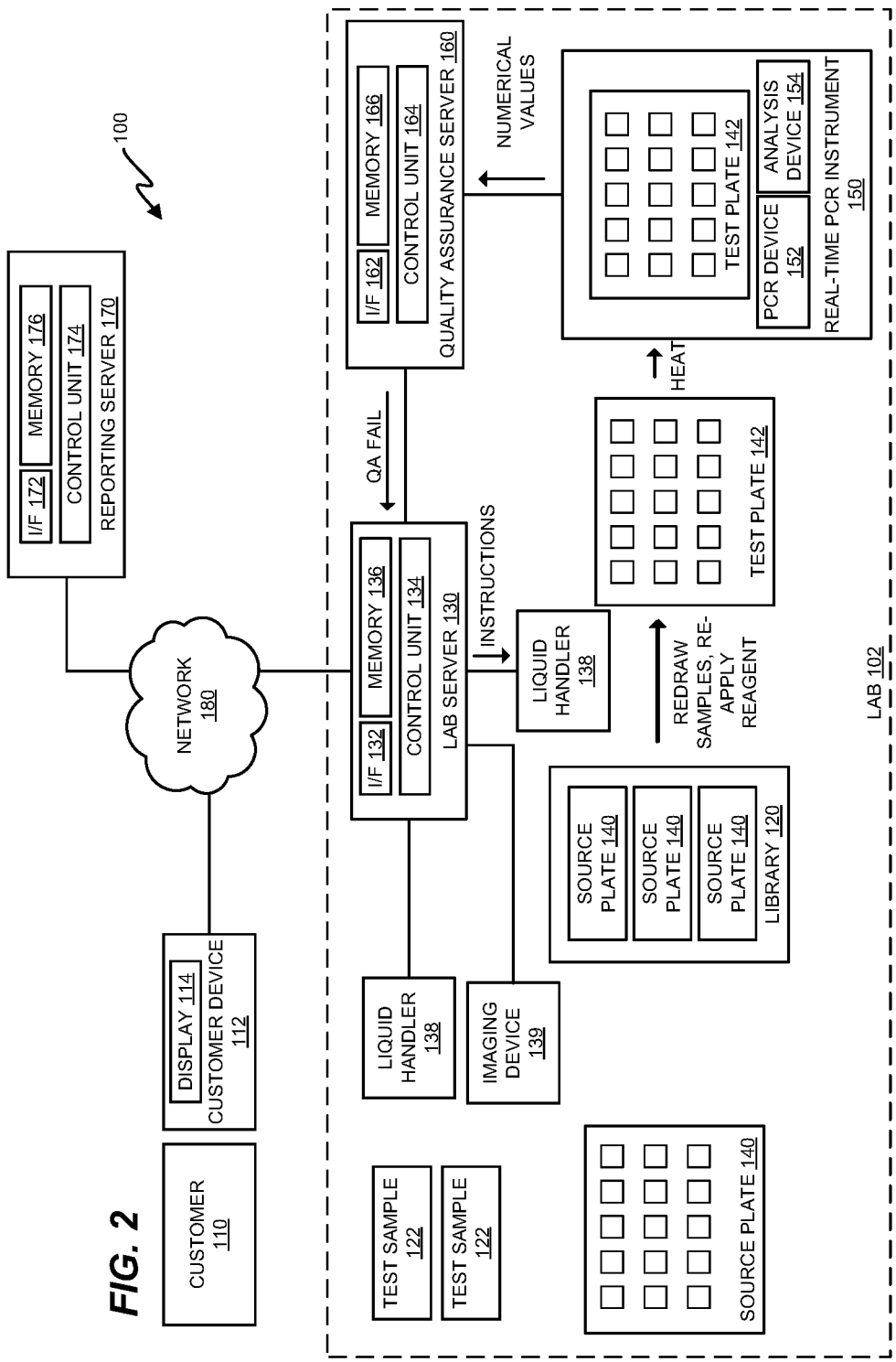
FIG. 2 is a block diagram depicting the high-throughput testing system of FIG. 1 performing re-testing in an illustrative embodiment.

FIG. 2 is a block diagram depicting the high-throughput testing system 100 of FIG. 1 performing re-testing in an illustrative embodiment. In this embodiment, control unit 164 of the quality assurance server 160 determines that the numerical values (e.g., fluorescence intensities) for a batch of test samples 122 are indicative of contamination, because the statistical likelihood of the arrangement of numerical values on the test plate 142 is below a threshold likelihood. Thus, the quality assurance server 160 transmits a QA fail message to the lab server 130. The control unit 134 of the lab server 130 then operates interface 132 to transmit instructions to requeue the test samples 122 for testing.

A liquid handler 138 proceeds to redraw the test samples 122 from one or more source plates 140 onto a new test plate 142. The liquid handler 138 further applies reagent to the new test plate 142. In one embodiment, the test samples 122 are re-arranged at the new test plate 142 before re-testing occurs. The new test plate 142 is then re-tested (e.g., via real-time PCR instrument 150), and numerical values acquired from re-testing are reported to the quality assurance server 160. This process of re-testing may iterate until a QA pass message is transmitted by the quality assurance server 160, until a technician decides to halt or bypass additional testing, or until a threshold number of re-tests has been performed.

Illustrative details of the operation of high-throughput testing system 100 will be discussed with regard to FIG. 3. Assume, for this embodiment, that test samples 122 have been stored in source plates 140 at library 120, and await testing for a disease state, such as a COVID disease state.

Figure 3:
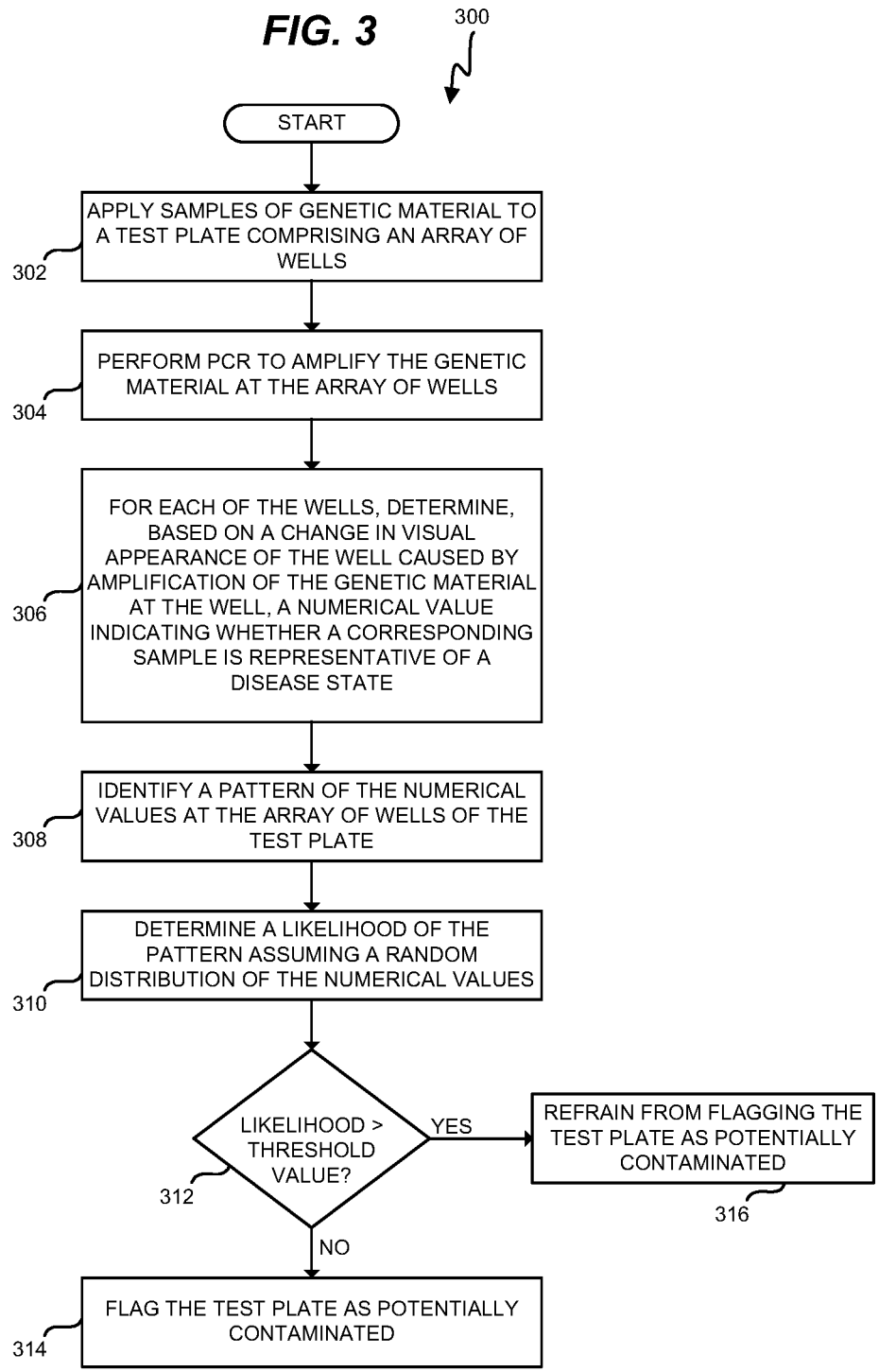
FIG. 3 is a flowchart depicting a method of operating a high-throughput testing system in an illustrative embodiment.

FIG. 3 is a flowchart depicting a method of operating a high-throughput testing system 100 in an illustrative embodiment. The steps of method 300 are described with reference to high-throughput testing system 100 of FIG. 1, but those skilled in the art will appreciate that method 300 may be performed in other systems. The steps of the flowcharts described herein are not all inclusive and may include other steps not shown. The steps described herein may also be performed in an alternative order.

Step 302 includes applying samples of genetic material to a test plate 142 comprising an array 144 of wells 146. In one embodiment, this comprises control unit 134 of lab server 130 providing instructions to a liquid handler 138 via interface 132, in order to transfer selected ones of the test samples 122 from one or more source plates 140 to a test plate 142 (as discussed above). In further embodiments, the control unit 134 provides additional instructions to add a reagent to each well 146 of the array 144 of the test plate 142. After the test plate 142 has been prepared with samples, it may be heated and placed into real-time PCR instrument 150 for amplification via PCR device 152 and testing via analysis device 154.

In step 304, PCR is performed upon test samples 122 at the test plate 142, to amplify genetic material within the array 144 of wells 146 at the test plate 142. This operation may be performed in accordance with standard PCR techniques. In this embodiment, each of the wells 146 undergoes PCR for the same amount of time, to ensure a consistent amount of amplification of genetic material within each well 146.

Upon completion of PCR, and during PCR, the reagent reacts with genetic material indicative of the disease state being tested for. That is, in one embodiment the reagent selectively reacts with (e.g., binds to), and generates fluorescence in response to reacting with, pieces of genetic material that correspond with the disease state, causing corresponding wells 146 to exhibit a visual change. For example, the reagent may selectively bind with genetic material uniquely associated with the SARS-CoV-2 virus, resulting in increased fluorescence within wells 146 that include such genetic material.

In step 306, for each of the wells 146, the analysis device 154 determines, based on a change in visual appearance of the well 146 caused by the amplification of the genetic material at the well 146, a numerical value indicating whether a corresponding test sample 122 is representative of a disease state. For example, in wells 146 where genetic material corresponding to the disease state is being amplified, the reagent may bind to the amplified genetic material and activate a fluorescent component, resulting in increased fluorescence of those wells. As used herein, in one embodiment, a test sample 122 is representative of a disease state if its numerical value indicates either a positive result or inconclusive result, while in another embodiment, a test sample 122 is representative of a disease state if its numerical value indicates a positive result.

In this embodiment, the numerical values determined by the analysis device 154 indicate fluorescence intensities at the wells 146, in fluorophore units. The fluorescence intensities are then scaled to a range (e.g., between zero and one, between zero and ten, etc.). The numerical values, together with identifying information indicating the locations of corresponding wells 146 at the test plate 142, are transmitted to interface 162 of the quality assurance server 160 for review.

In step 308, control unit 164 identifies a pattern of the numerical values at the array 144 of wells 146 of the test plate 142. A pattern comprises an arrangement of numerical values of the array 144 at the test plate 142. In this embodiment, the control unit 164 of the quality assurance server 160 filters out numerical values from the pattern that are below a first limit (e.g., below the threshold at which a result is inconclusive, or below the threshold at which a result is positive), prior to determining the likelihood of the pattern. This may result in a pattern comprising an arrangement of numerical values that are positive and/or are inconclusive, but not negative.

In step 310, the control unit 164 determines a likelihood of the pattern assuming a random distribution of the numerical values. That is, the control unit 164 determines the likelihood that a similar pattern would be found if the numerical values were arranged randomly at the test plate 142. This likelihood may be determined assuming a Bernoulli distribution of the numerical values, or other suitable random distribution.

In one embodiment, the control unit 164 identifies motifs within the pattern that are representative of the disease state. A motif comprises a contiguous geometric arrangement of numerical values and/or diagnostic results. That is, a motif forms a shape, and each position within the shape of the motif is assigned a numerical value, range of numerical values, diagnostic result, or combination of diagnostic results. For example, a motif may comprise a contiguous two dimensional (2D) grouping of diagnostic results that are representative of the disease state. By sweeping a motif across the pattern, and determining a number of times that numerical values or diagnostic results of the pattern match those of the motif, a count of instances of the motif may be acquired for a given array 144.

Different motifs may comprise different shapes (e.g., squares, rectangles, lines, elbows, zig-zags, etc. having predefined sizes). In one embodiment, the motifs comprise shapes selected from the group consisting of: squares that are two samples wide and two samples long, rectangles that are one sample wide and four samples long, or rectangles that are four samples wide and one sample long. Furthermore, different motifs may exhibit different combinations of numerical values and/or diagnostic results. This means that motifs may comprise shapes made up of different combinations of results that are positive, inconclusive, and/or negative. Thus, a motif may comprise a rectangle that is one sample high and six samples long, which includes six samples that are positive or inconclusive, any combination of five samples that are positive or inconclusive and one sample that is negative, any combination of four samples that are positive or inconclusive and two samples that are negative, etc.

Example motifs may therefore include a grouping of five numerical values representative of the disease state and one numerical value representative of a disease-free state within a rectangle that is one sample wide and six samples long, and a grouping of five numerical values representative of the disease state and one numerical value representative of a disease-free state within a rectangle that is six samples wide and one sample long, etc.

For each motif, the control unit 164 of the quality assurance server 160 may determine a number of instances of the motif in the pattern, and determine a probability of that number of instances of the motif existing within the array 144 of the test plate 142. That is, the controller 164 determines a likelihood that the counted number of instances of a motif within the pattern would appear within the array 144. The controller 164 may count instances of a motif in the pattern by placing the motif over each possible location that the motif could occupy in the pattern. At each location, numerical values for the pattern at that location are compared to the motif to see if the numerical values match those required by the motif. If so, an instance of the motif is detected at that location.

In one embodiment, the probability of a given instance of a motif appearing is based on the number of wells 146 at the array 144 of the test plate 142, as well as a fraction p of the wells 146 that are representative of the disease state (e.g., that indicate a positive result or inconclusive result). Under the assumption that the positive results and/or inconclusive results are distributed randomly, each well 146 in the array 144 of the test plate 142 is expected to be positive and/or inconclusive with probability p (i.e., distributed as a Bernoulli random variable with a success rate of p). The value p may be determined for each test plate 142, or may be defined globally for the laboratory 102 as desired. The value p may also be referred to a positivity rate.

For any given motif, the probability of the motif is determined by the positivity rate p in combination with a size of the motif. This probability of the motif is referred to as a(p). That is, for a motif comprising fully positive and/or inconclusive results, the likelihood a(p) is equal to $p^n$ where n is the number of wells represented by the motif. For a motif comprising some positive and/or inconclusive results as well as some negative results, the likelihood a(p) is equal to $(^m_r)p^m(1-p)^r$, wherein m is the number of wells having positive and/or inconclusive results, and r is the number of wells having negative results.

With the dimensions of a motif being known, and a size of the array 144 of the test plate 142 (e.g., a number of rows and columns in the array 144 of wells 146) being known, there are N opportunities for the motif to appear on that array 144 of the test plate 142. For example, on a test plate 142 having an array 144 of three hundred and eighty-four wells 146, comprising sixteen columns and twenty-four rows, there are three hundred and forty-five instances of two-by-two groups of wells 146 (corresponding to fifteen possible columnar positions multiplied by twenty-three possible row-wise positions for the motif), and hence three hundred and forty-five instances for a corresponding motif to be detected. Thus, N equals three hundred and forty-five.

Based on this information, T, the expected number of instances of a motif of a given shape on the array 144 of the test plate 142, given the positivity rate p, is a binomial random variable with N number of trials, each with probability a(p) of success, as shown in formula (1) below.

$$T \sim \text{Binomial}(N, a(p)) \quad (1)$$

Given an observed count t of instances of the motif on a test-plate, a p-value P for that motif is determined according to formula (2) below.

$$P\{T=t\} = (^N_t)a(p)^t[1-a(p)]^{N-t} \quad (2)$$

With the likelihood of a number of instances of a specific motif being known via the formulas above, the concept may be generalized to apply to multiple motifs, indexed by i. In this instance, three motifs are considered, resulting in i ranging from one to three. Given a positivity rate p, the probability of motif i can be defined as $a_i(p)$ and its count/tally on any test plate 142 can be defined as $T_i$.

Depending on the shape of the motif, the number of opportunities for the motif to appear on an array 144 of a test plate 142 differ. Hence, the value N for each motif may be calculated as a separate $N_i$. In this environment, formula (1) above becomes formula (3) below.

$$T_i \sim \text{Binomial}(N_i, a_i(p)) \quad (3)$$

With this in mind, the overall p-value that incorporates the improbability of all motifs chosen for review is given by formula (4) below.

$$\min_i\{P\{T_i=t_i\}\} \quad (4)$$

The number $\min_i$ represents the likelihood of the pattern appearing randomly. When an array 144 of a test plate 142 has a non-random distribution of positives, $\min_i$ is expected to be particularly low. Furthermore, the more non-random the pattern of positives, the smaller $\min_i$ becomes. Because contamination of a test plate 142 is often expected to be caused by liquid spilling between adjacent wells 146, a non-random pattern of positive and/or inconclusive results is strongly correlated with contamination. That is, systemic issues with liquid handling may result in clusters of positive specimens that are localized to specific regions of the test plate 142.

In step 312, control unit 164 proceeds to determine whether the likelihood determined in step 310 exceeds a predetermined threshold value in memory 166. The predetermined threshold value may comprise, for example, a p-value of 0.001, 0.00001, or less. In the event that the likelihood is greater than the threshold value, the diagnostic results are consistent with expectations (i.e., within a normal range), and in step 316 control unit 164 refrains from flagging the test plate 142 as potentially contaminated. This may be performed, for example, by transmitting a QA pass message to the lab server 130. Upon receiving the QA pass message, the lab server 130 is permitted to report the diagnostic result (e.g., positive, negative, or inconclusive) for each of the wells 146 of the test plate 142 to the reporting server 170 for distribution to customer devices 112.

Alternatively, in the event that the likelihood is less than the threshold value, the diagnostic results are inconsistent with expectations (i.e., outside of a normal range), and in step 314 control unit 164 flags the test plate 142 as potentially contaminated. This may be performed, for example, by transmitting a QA fail message to the lab server 130.

In some embodiments, the QA fail message comprises an implicit instruction to re-test the test samples 122, or is accompanied by an explicit instruction to re-test the test samples 122. In such an embodiment, control unit 134 of the lab server 130 provides new instructions to a liquid handler 138, which applies the test samples 122 to a new test plate 142 comprising an additional array 144 of wells 146. An arrangement of the test samples 122 on the new test plate 142 may be selected so that it is different from an arrangement of the test samples 122 on the original test plate 142.

Method 300 provides a substantial advantage over prior techniques because it enables rapid and consistent detection of test plates 142 that exhibit an abnormal arrangement of values representative of a disease state. By performing this operation automatically, rigorously, and statistically, method 300 eliminates the possibility for human error while also dramatically increasing the rate at which quality assurance is performed. This in turn increases the overall operational speed of the high-throughput testing system 100, which increases throughput while also reducing labor costs.

With a discussion provided above of the general operations of biological testing and quality assurance, FIGS. 4-9 depict an implementation of the quality assurance process performed by a control unit 164 of the quality assurance server 160 in an illustrative embodiment.

Figure 4:
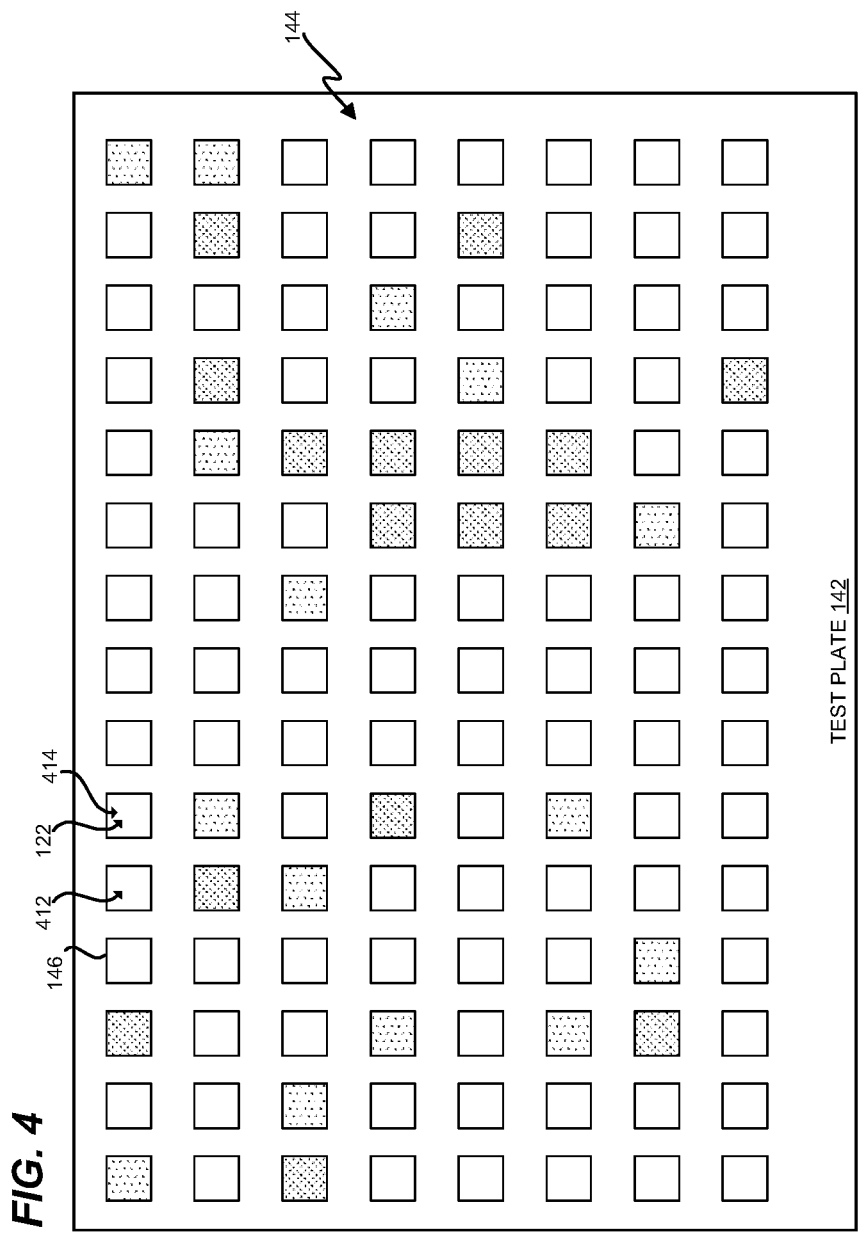
FIG. 4 depicts a test plate of wells that are each filled with a solution comprising a test sample and a reagent in an illustrative embodiment.

FIG. 4 depicts a test plate 142 of wells 146 that are each filled with a solution 412 comprising a test sample 122 and a reagent 414 in an illustrative embodiment. In this embodiment, a degree of reaction of the reagent 414 with the test samples 122 in the wells 146 results in a visual change in appearance. Thus, in wells 146 where the reagent 414 did not react, no visual change is apparent. In other wells 146 of the array 144, the degree of visual change is linked with a degree of reaction of the reagent 414 with a corresponding test sample 122.

FIG. 5 depicts numerical values 500 assigned to an array 144 of wells 146 that have been analyzed in an illustrative embodiment. The numerical values 500 each indicate an amount of visual change (e.g., a fluorescence intensity) detected within a corresponding well 146. In this embodiment, each numerical value 502 has been scaled to a range between zero and ten. In further embodiments, the numerical values 502 may be scaled to any suitable range, or scaling may be foregone entirely.

FIG. 6 depicts a filtered version of the numerical values 500 of FIG. 5 in an illustrative embodiment. In this embodiment, numerical values below four indicate a negative result (i.e., an absence of the disease state being tested). Meanwhile, numerical values between four and five indicate an inconclusive result, and numerical values greater than five indicate a positive result (i.e., the presence of the disease state being tested). In this embodiment, the filtering process performed by control unit 164 filters out numerical values that indicate a negative result, by setting all numerical values below four to zero.

FIG. 7 depicts the numerical values of FIG. 6 converted to hits 710 and misses 720 in an illustrative embodiment. In this embodiment, the conversion process comprises generating a hit table 700, wherein each non-zero number remaining among the numerical values is converted to a value of one. Each value of zero in the hit table 700 indicates a miss 720 (e.g., a negative result), and each value of one in the hit table 700 indicates a hit 710 representative of the disease state (e.g., a positive or inconclusive result). The resulting pattern 730 of hits 710 is suitable for statistical analysis by matching to one or more motifs. This technique of generating a binary map of hits and misses reduces processing burden during quality control analysis. However, in further embodiments, the use of a hit table may be foregone entirely.

Figure 8:
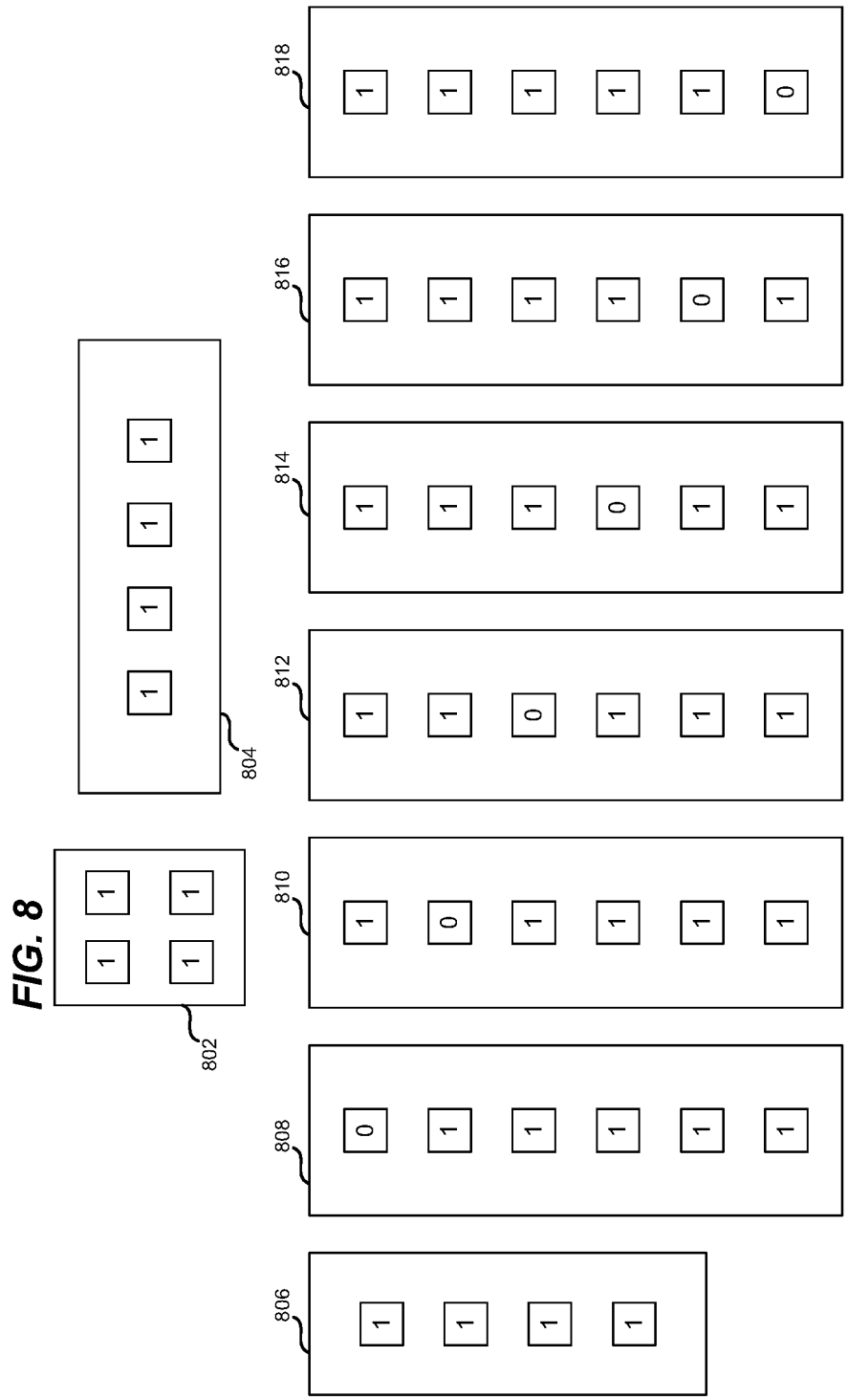
FIG. 8 depicts a series of motifs used to determine the likelihood of a pattern of hits in an illustrative embodiment.

FIG. 8 depicts a series of motifs 802-818 used to determine the likelihood of a pattern of hits in an illustrative embodiment. In this embodiment, each motif comprises a different shape and/or size of a combination of hits and misses, and is associated with a different likelihood of occurrence. The likelihood of occurrence of each motif is a function of the likelihood of each hit and/or miss within the motif. For example, if a positive result and/or inconclusive result is expected with a likelihood of twenty percent for each well, then motif 802 exhibits a likelihood of 0.16 percent for any two-by-two cluster of numerical values.

In further embodiments, the likelihood of a positive result and/or inconclusive result is set equal to the likelihood for the current test plate 142. That is, the likelihood is set to the sum of positive results and inconclusive results, divided by the number of wells 146 on the test plate 142. In still further embodiments, the likelihood of a positive result and/or inconclusive result is determined empirically and set to a constant value for all test plates 142. In this embodiment, motifs 808, 810, 812, 814, 816, and 818 each include a miss at a predetermined location. Including a miss within a motif this facilitates a form of "fuzzy" matching that may be desirable in certain instances.

Figure 9:
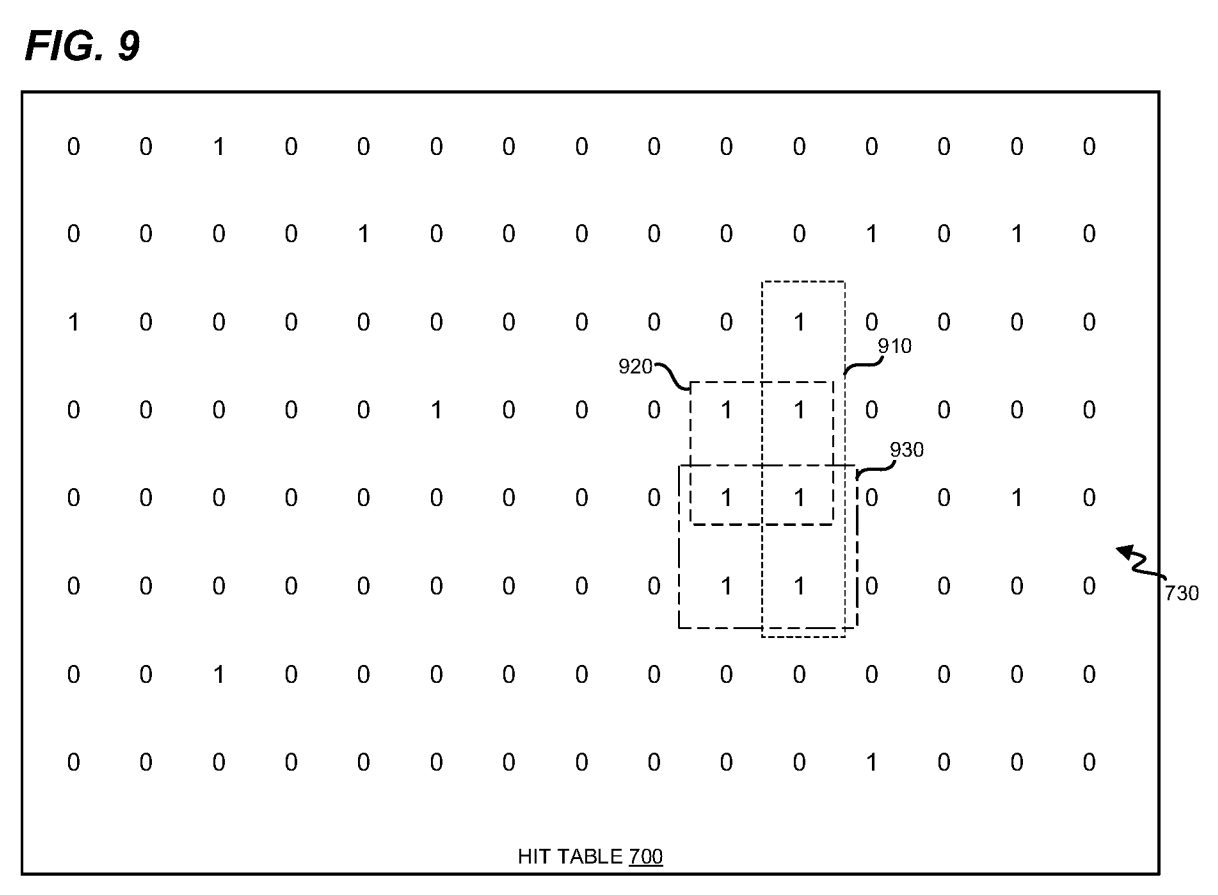

FIG. 9 depicts the motifs of FIG. 8 being matched against a pattern 730 of hits in an illustrative embodiment. In this embodiment, motif 802 is found within the pattern 730 at location 920 and location 930, while motif 806 is found within the pattern 730 at location 910. Given that the test plate 142 has eight rows and fifteen columns, a likelihood of motif 802 occurring twice within the pattern 730 may be determined, as well as a likelihood of motif 806 occurring once within the pattern 730. An overall likelihood across all motifs may then be determined, and compared against a threshold value for quality assurance purposes as discussed above.

Figure 10:
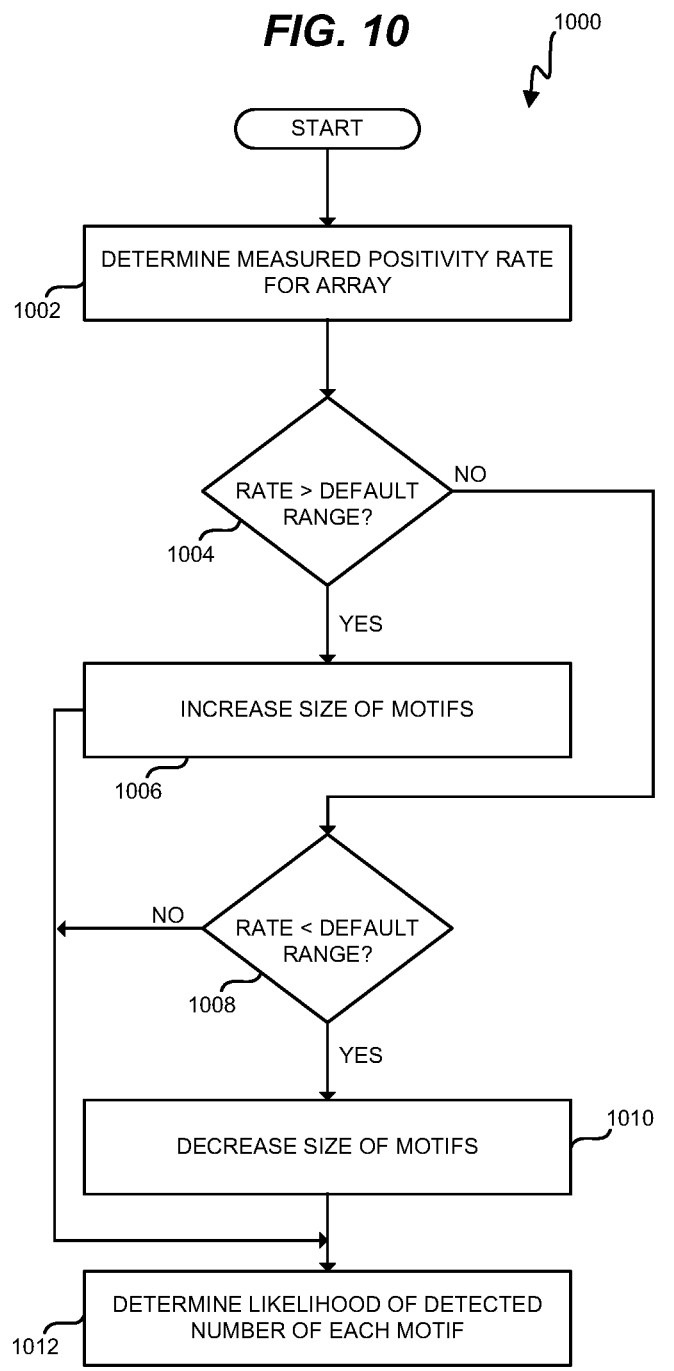
FIG. 10 is a flowchart depicting a method for controlling the size of motifs utilized to analyze a test plate, based on an amount of positivity detected for the test plate in an illustrative embodiment.

FIG. 10 is a flowchart depicting a method 1000 for controlling the size of motifs utilized to analyze a test plate 142, based on an amount of positivity detected for the test plate 142 in an illustrative embodiment. Controlling motif size results in a technical benefit by ensuring that the statistical methods of quality assurance applied to a test plate 142 are tailored to the positivity rate of that test plate 142.

Step 1002 includes control unit 164 determining a measured positivity rate for an array 144 of wells 146 at the test plate 142. Depending on embodiment, the positivity rate may be set equal to the sum of positive results and inconclusive results, divided by the number of wells 146 on the test plate 142, or may be set equal to the number of positive results divided by the number of wells 146 on the test plate 142.

In step 1004, the control unit 164 determines whether the measured positivity rate is greater than an expected range of positivity rates (e.g., between five and forty percent) stored in memory 166. If the rate is greater, then in step 1006, control unit 164 increases sizes of motifs utilized. For example, control unit 164 may increase motif size from a range of four to five contiguous hits, to a range of five to six contiguous hits, by increasing a minimum number of contiguous positions within a motif by one, etc.

The purpose of increasing the sizes of the motifs is to reduce the likelihood of each motif being found within a pattern. When the positivity rate for a test plate 142 is higher than expected, the probability of a motif existing within the pattern is increased. By increasing a size of the motif, this probability is decreased. Thus, the overall likelihood of finding a motif within the pattern may be kept within a desired range. This accomplishes a technical benefit by enabling p-values to be precisely measured for the specific test plate 142 being analyzed.

If the measured positivity rate is not greater than the expected range, in step 1008 the control unit 164 determines whether the measured positivity rate is lower than the expected range of positivity rates. If so, in step 1010 the control unit 164 proceeds to reduce sizes of motifs utilized. For example, control unit 164 may reduce motif size from a range of four to five contiguous hits, to a range of three to four contiguous hits, by decreasing a maximum number of contiguous positions within a motif by one, etc.

The purpose of reducing the sizes of the motifs is to increase the likelihood of each motif being found within a pattern. When the positivity rate for a test plate 142 is lower than expected, the probability of a motif existing within the pattern is reduced. By shrinking a size of the motif, this probability is increased. Thus, the overall likelihood of finding a motif within the pattern may be kept within a desired range. This accomplishes a technical benefit by enabling p-values to be precisely measured for the specific test plate 142 being analyzed.

With motif size adjusted, in step 1012 the control unit 164 proceeds to determine a likelihood of a detected number of instances of each motif within the pattern being analyzed. This information is then utilized to determine an overall likelihood of the pattern 730 of hits found at the test plate 142.

Method 1000 provides a technical benefit over prior systems and techniques, because it ensures that motifs are scaled in a manner that allows for accurate detection of hit clustering indicative of contamination, even for test plates 142 that exhibit non-standard positivity rates. This reduces the number of instances where a test plate 142 would be subject to an erroneous QA pass or QA fail result, and hence increases overall accuracy and reliability of the QA process.

Figure 11:
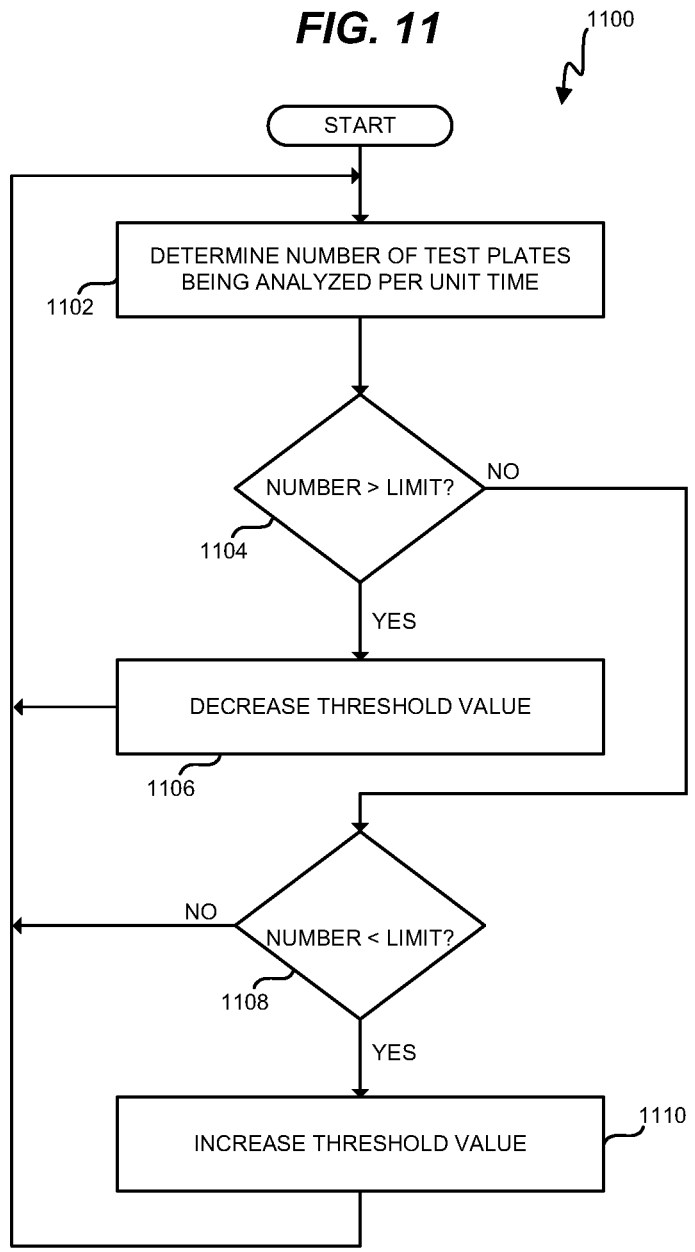
FIG. 11 is a flowchart depicting a method for dynamically adjusting a threshold value for re-testing, based on a rate at which test plates are analyzed by a high-throughput testing system in an illustrative embodiment.

FIG. 11 is a flowchart depicting a method 1100 for dynamically adjusting a threshold value for re-testing, based on a rate at which test plates 142 are analyzed by a high-throughput testing system 100 in an illustrative embodiment.

In step 1102, the control unit 164 determines a number of test plates 142 being analyzed per unit time. In one embodiment, this comprises transmitting a query to lab server 130 and awaiting a reply. In a further embodiment, this comprises determining a number of test plates 142 for which numerical values have been received from one or more analysis devices 154 at the laboratory 102 over the last hour, day, week, etc. If the number of test plates 142 is lower than expected, then more time may be available at the high-throughput testing system 100 to ensure accuracy. Alternatively, if the number of test plates 142 is higher than expected, then less time may be available for such purposes.

In step 1104, the control unit 164 determines whether the volume is greater than a predefined limit (e.g., between ten and twenty plates per hour) stored in memory 166. If the volume is greater, then in step 1106 the threshold value is decreased. This means that more test plates 142 will exhibit likelihoods greater than the threshold value, and will not be flagged as being potentially contaminated (and hence in need of re-testing). Although the threshold value may be reduced via this process, it may never be reduced below the quality standards set in place for the high-throughput testing system 100.

If the volume is not greater than the predefined limit, then processing continues to step 1108. In step 1108, the control unit 164 determines whether the volume is less than the predefined limit. If so, then the threshold value is increased in step 1110. This means that more test plates 142 will exhibit likelihoods less than the threshold value, and will be flagged as being potentially contaminated (and hence in need of re-testing). If not, then processing returns to step 1102, which is performed periodically to update the threshold value.

In further embodiments, memory 166 may store a table or other data structure in memory indicating a variety of threshold values for a variety of volumes of test plates 142. In this manner, the control unit 164 may control the quality assurance process at a high level of granularity.

Method 1100 provides a technical benefit over prior systems and techniques, because the choice of threshold value discussed in method 1100 reflects a tradeoff between minimizing re-processing and tolerating false positives in the testing environment. By dynamically adjusting the threshold value based on a rate at which biological testing is performed, the tradeoff can be adjusted to ensure a desired combination of both accuracy and speed. For example, during periods of higher volume, where the re-processing of test plates 142 is costly because they delay the return of results, the threshold value can be more permissive. Conversely, when the high-throughput testing system 100 has excess capacity, the threshold value can be more stringent, allowing for more accurate results without a significant impact on turn-around time. This type of calibration is not possible to achieve via human visual review of the test plates 142.

Figure 12:
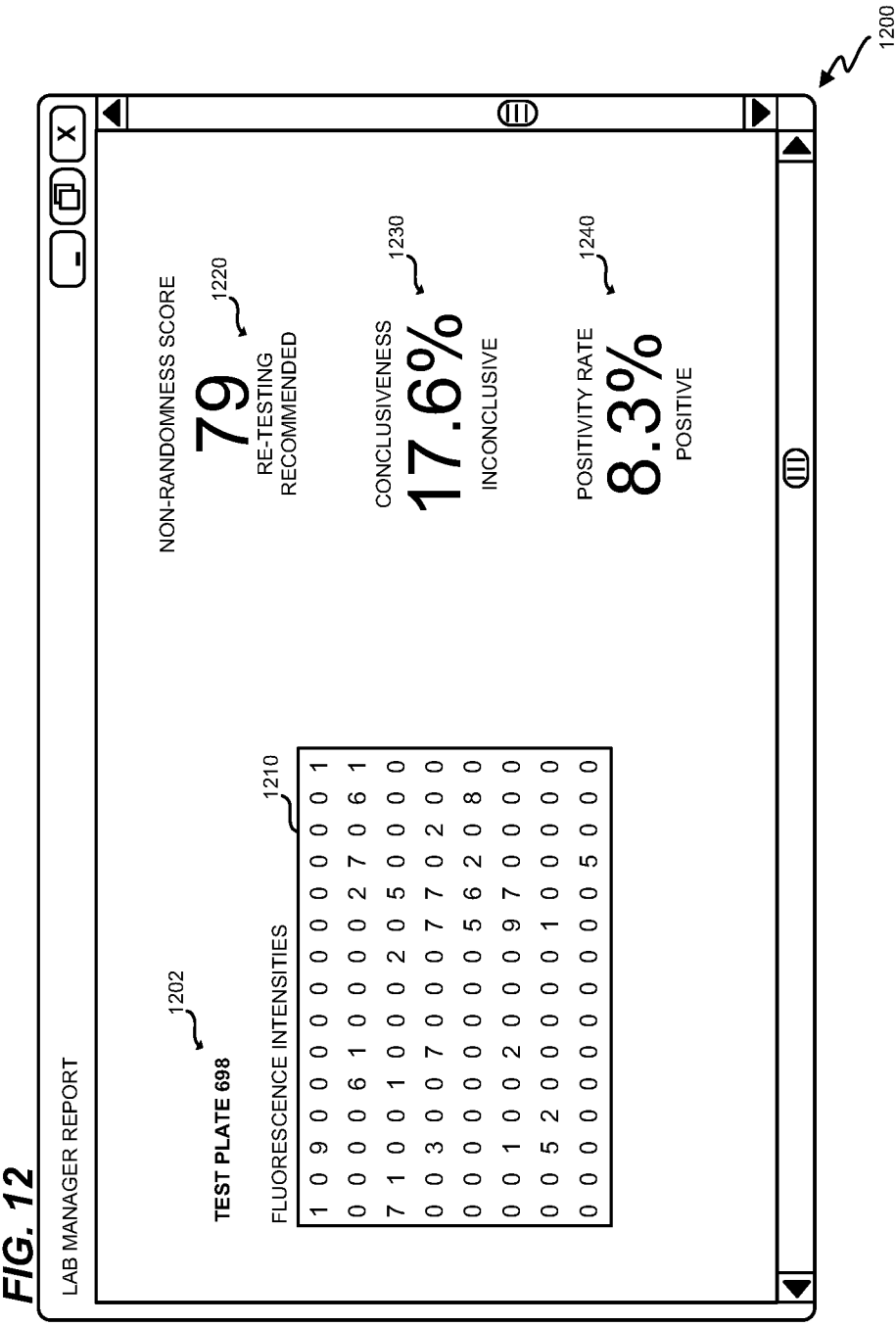
FIG. 12 depicts a report for review by a laboratory technician in an illustrative embodiment.

FIG. 12 depicts a report 1200 for review by a laboratory technician in an illustrative embodiment. Report 1200 may be generated, for example, by control unit 164 of the quality assurance server 160, and then forwarded to the lab server 130 for presentation at a display (not shown). This enables a laboratory technician to rapidly review the results for a test plate 142 and determine whether additional measures are necessary to ensure both rapid and accurate operation of laboratory 102.

In this embodiment, the report 1200 includes an identifier 1202 for the test plate 142, as well as a graphical arrangement of results 1210 for a specific test plate 142. The results 1210 may be provided as numerical values, or graphically (e.g., as a series of positions colored according to numerical value). The report 1200 also includes a non-randomness score 1220 scaled from zero to one hundred, with one hundred being total non-randomness and zero being total randomness. Control unit 164 may compute the non-randomness score 1220 by scaling a p-value determined for the test plate 142. For example, the non-randomness score may equal the inverse of the p-value divided by one thousand or ten thousand, then capped at one hundred. In this embodiment, controller 164 recommends re-testing if the non-randomness score 1220 is above a predefined threshold. Hence, the non-randomness score is accompanied by a textual descriptor indicating whether or not re-testing is recommended.

In this embodiment, report 1200 also includes a technical assessment of test conclusiveness 1230, and a positivity rate 1240. The test conclusiveness 1230 indicates a percentage of test samples 122 at the test plate 142 associated with an inconclusive result. If the percentage rises above a threshold value, this may be indicative of a poorly calibrated PCR process. Thus, if the percentage is greater than the threshold value, controller 164 may include a recommendation to re-calibrate PCR at the report 1200.

The positivity rate 1240 indicates a percentage of test samples 122 at the test plate 142 associated with a positive result. If the percentage exits an expected range (e.g., five to forty percent), this may be indicative of a poorly calibrated PCR process, failure of the reagent, or systemwide contamination. Thus, if the percentage is outside of the expected range, controller 164 updates the report 1200 to recommend PCR recalibration.

Based on report 1200, a laboratory technician may take steps to alter conditions at the laboratory 102. For example, the laboratory technician may recalibrate PCR processes at one or more real-time PCR instruments 150, replace the existing batch of reagent used by the liquid handlers 138, clean the liquid handlers 138, adjust a temperature of the library 120, and/or take other measures. In this manner, report 1200 provides a technical benefit by helping to ensure that the laboratory 102 rapidly detects and responds to conditions which could impact throughput or accuracy.

EXAMPLES

In the following examples, additional processes, systems, and methods are described in the context of a high-throughput testing system 100. Assume, for this embodiment, that high-throughput testing system 100 is presently receiving deliveries of test samples 122 from customers 110 that comprise health care networks serving tens of thousands of patients. The test samples 122 are received, unpacked, applied to source plates 140 by the thousands via one or more liquid handlers 138, and kept in library 120 for long-term storage. Lab server 130 stores identifying information for each test sample 122, as well as a location of each test sample 122 at library 120, in memory 136. As test samples 122 are received for testing, lab server 130 prepares test plates 142 for biological testing and analysis.

In this embodiment, lab server 130 ensures that each test plate 142 is filled with test samples 122 before undergoing testing, and ensures that each test plate 142 receives reagent within each well 146. Test plates 142 are distributed to multiple real-time PCR instruments 150, which each perform PCR, then analyze visual changes in wells 146 via an analysis device 154. Analysis devices 154 transmit numerical values to quality assurance server 160 for review, along with the locations (e.g., row and column) of corresponding wells 146.

The numerical values for each test plate 142 are filtered by control unit 164 and converted into hit tables, and the resulting patterns are matched against motifs stored in memory 166. If the number of matches of motifs varies from expectations, the likelihood of the pattern is below normal. If this likelihood for a test plate 142 is below a threshold value stored in memory 166, it is then flagged as potentially contaminated and re-tested. During this process, many test plates 142 may be handled at once asynchronously and/or in parallel, such that the re-testing of samples for a single test plate 142 does not delay the testing of other test plates 142 traveling through the high-throughput testing system 100. Diagnostic results (textual labels of "positive," "negative," "inconclusive," etc.) and/or underlying numerical values for test plates 142 that have passed quality assurance are sent onward to reporting server 170.

The reporting server 170 batches the diagnostic results for transmission to corresponding customer devices 112 on a periodic basis, or updates a report in real-time for access by customer devices 112. As a part of this process, access to reports and results is secured by an authentication protocol and/or login credentials particular to personnel for each customer 110, and diagnostic results for the test samples 122 are maintained privately for the customers 110 that provided those test samples 122. Thus, each customer 110 has access only to diagnostic results for test samples 122 provided by that customer 110.

Any of the various computing and/or control elements shown in the figures or described herein may be implemented as hardware, as a processor implementing software or firmware, or some combination of these. For example, an element may be implemented as dedicated hardware. Dedicated hardware elements may be referred to as "processors," "controllers," or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Figure 13:
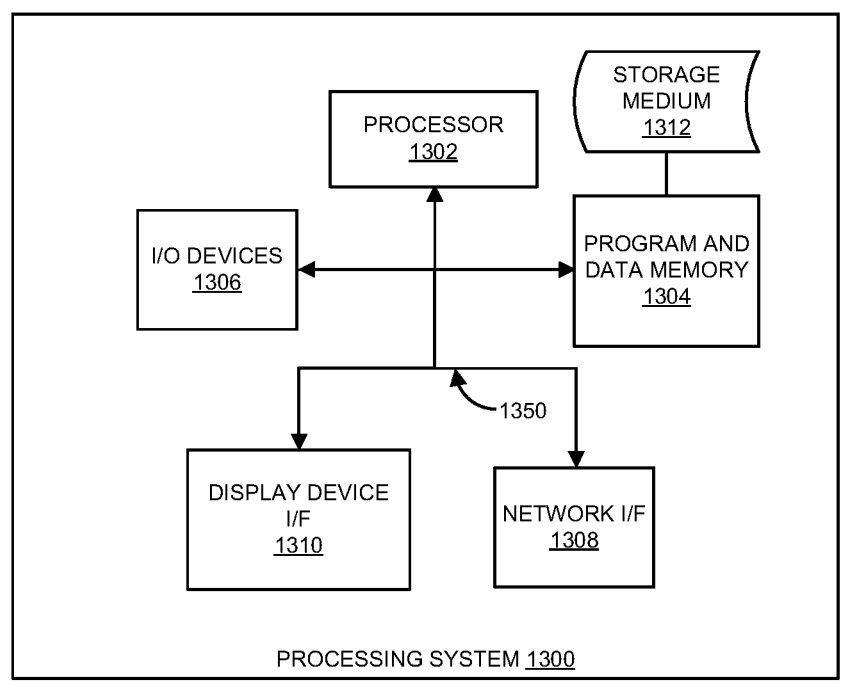
FIG. 13 depicts an illustrative computing system operable to execute programmed instructions embodied on a computer readable medium.

In one particular embodiment, instructions stored on a computer readable medium direct a computing system of any of the devices and/or servers discussed herein, such as quality assurance server 160, to perform the various operations disclosed herein. FIG. 13 depicts an illustrative computing system 1300 operable to execute a computer readable medium embodying programmed instructions. Computing system 1300 is operable to perform the above operations by executing programmed instructions tangibly embodied on computer readable storage medium 1312. In this regard, embodiments may utilize instructions (e.g., code) accessible via computer-readable medium 1312 for use by computing system 1300 or any other instruction execution system. For the purposes of this description, computer readable medium 1312 comprises any physical media that is capable of storing a program for use by computing system 1300. For example, computer-readable medium 1312 may be an electronic, magnetic, optical, electromagnetic, infrared, semiconductor device, or other non-transitory medium. Examples of computer-readable medium 1312 include a solid-state memory, a magnetic tape, a removable computer diskette, a random access memory (RAM), a read-only memory (ROM), a rigid magnetic disk, and an optical disk. Current examples of optical disks include Compact Disk-Read Only Memory (CD-ROM), Compact Disk-Read/Write (CD-R/W), Digital Video Disc (DVD), and Blu-Ray Disc.

Computing system 1300, which stores and/or executes the instructions, includes at least one processor 1302 coupled to program and data memory 1304 through a system bus 1350. Program and data memory 1304 include local memory employed during actual execution of the program code, bulk storage, and/or cache memories that provide temporary storage of at least some program code and/or data in order to reduce the number of times the code and/or data are retrieved from bulk storage (e.g., a spinning disk hard drive) during execution.

Input/output or I/O devices 1306 (including but not limited to keyboards, displays, touchscreens, microphones, pointing devices, etc.) may be coupled either directly or through intervening I/O controllers. Network adapter interfaces 1308 may also be integrated with the system to enable computing system 1300 to become coupled to other computing systems or storage devices through intervening private or public networks. Network adapter interfaces 1308 may be implemented as modems, cable modems, Small Computer System Interface (SCSI) devices, Fibre Channel devices, Ethernet cards, wireless adapters, etc. Display device interface 1310 may be integrated with the system to interface to one or more display devices, such as screens for presentation of data generated by processor 1302.

What is claimed is:

1. A system for controlling quality by identifying potential contamination at test plates, the system comprising:
    a liquid handler configured to apply samples of genetic material to a test plate comprising an array of wells;
    a Polymerase Chain Reaction (PCR) device configured to amplify the genetic material at the array of wells for reaction with a reagent at the wells, wherein the reagent selectively reacts with portions of the genetic material that correspond with a disease state;
    an analysis device configured to determine a numerical value for each well of the wells based on a change in visual appearance caused by the amplification of the genetic material at the well, wherein the numerical value indicates whether a corresponding sample at the well is representative of the disease state; and a quality assurance server, comprising a memory and a control unit having a processor, configured to receive numerical values for the wells and location information indicating a location of each of the wells on the test plate, and to identify a pattern of the numerical values based on the location information, wherein the pattern comprises an arrangement of the numerical values of the array of wells at the test plate;

wherein the quality assurance server is further configured to determine a statistical likelihood of the pattern of the numerical values assuming a random distribution of the numerical values;

wherein, when the statistical likelihood is less than a threshold value, the quality assurance server is further configured to determine that the arrangement of the numerical values of the array of wells at the test plate is statistically improbable and indicative of a potential contamination of liquid spilling between adjacent ones of the wells, and to flag the test plate as potentially contaminated.

2. The system of claim 1 wherein:

the quality assurance server is further configured to identify motifs that each comprise a predefined two dimensional (2D) grouping of numerical values; and the quality assurance server is further configured, for a motif of the motifs, to sweep the motif across the pattern of the numerical values, to determine a number of times that the grouping of numerical values of the motif matches the numerical values in the pattern, and to determine a likelihood of the motif occurring the number of times, wherein an overall likelihood across the motifs comprises the statistical likelihood of the pattern of the numerical values occurring on the test plate.

3. The system of claim 2 wherein:

the motifs are selected from the group consisting of: 2×2 squares that contain four numerical values representative of the disease state, 1×4 rectangles that contain four numerical values representative of the disease state, 4×1 rectangles that contain four numerical values representative of the disease state, a grouping of five numerical values representative of the disease state within a 1×6 rectangle, and a grouping of five numerical values representative of the disease state within a 6×1 rectangle.

4. The system of claim 2 wherein:

the motifs comprise distinct shapes.

5. The system of claim 1 wherein:

the quality assurance server is further configured to filter out the numerical values from the pattern that are below a limit prior to determining the statistical likelihood of the pattern of the numerical values occurring on the test plate.

6. The system of claim 1 wherein:

when the statistical likelihood is less than the threshold value, the quality assurance server is further configured to transmit an instruction to re-test the samples, and the liquid handler is further configured to apply the samples to a new test plate, wherein an arrangement of the samples on the new test plate is different from an arrangement of the samples on the test plate.

7. The system of claim 1 wherein:

the reagent selectively reacts with the portions of the genetic material that correspond with the disease state to generate fluorescence; and the analysis device is further configured to determine the numerical value for each of the wells that quantifies a fluorescence intensity of the well.

8. The system of claim 2 wherein:

the quality assurance server is further configured to scale the motifs based on a positivity rate of the test plate.

9. The system of claim 1 wherein:

the quality assurance server is further configured to adjust the threshold value based on a volume of test plates being analyzed by the analysis device per unit time.

10. The system of claim 1 wherein:

the disease state is a Coronavirus Disease (COVID) disease state, the reagent comprises a fluorescent reporter molecule, and the numerical values indicate fluorescence intensities, and the quality assurance server is further configured to compare the numerical values to distinct ranges of fluorescence intensities that each correspond with a different diagnostic result relating to COVID.

11. A method for controlling quality by identifying potential contamination at test plates, the method comprising:

applying samples of genetic material to a test plate comprising an array of wells;

performing Polymerase Chain Reaction (PCR) to amplify the genetic material at the array of wells for reaction with a reagent at the wells, wherein the reagent selectively reacts with portions of the genetic material that correspond with a disease state;

determining, at an analysis device, a numerical value for each well of the wells based on a change in a visual appearance caused by the amplification of the genetic material at the well, wherein the numerical value indicates whether a corresponding sample at the well is representative of the disease state;

receiving, at a quality assurance server, numerical values for the wells and location information indicating a location of each of the wells on the test plate;

identifying, at the quality assurance server, a pattern of the numerical values based on the location information, wherein the pattern comprises an arrangement of the numerical values of the array of wells at the test plate;

determining, at the quality assurance server, a statistical likelihood of the pattern of the numerical values assuming a random distribution of the numerical values; and when the statistical likelihood is less than a threshold value, determining, at the quality assurance server, that the arrangement of the numerical values of the array of wells at the test plate is statistically improbable and indicative of a potential contamination of liquid spilling between adjacent ones of the wells; and flagging the test plate as potentially contaminated.

12. The method of claim 11 further comprising:

identifying motifs that each comprise a predefined two dimensional (2D) grouping of numerical values;

for a motif of the motifs, sweeping the motif across the pattern of the numerical values;

determining a number of times that the grouping of numerical values of the motif matches the numerical values in the pattern; and determining a likelihood of the motif occurring the number of times, wherein an overall likelihood across the motifs comprises the statistical likelihood of the pattern of the numerical values occurring on the test plate.

13. The method of claim 12 wherein:
the motifs are selected from the group consisting of: 2×2 squares that contain four numerical values representative of the disease state, 1×4 rectangles that contain four numerical values representative of the disease state, 4×1 rectangles that contain four numerical values representative of the disease state, a grouping of five numerical values representative of the disease state within a 1×6 rectangle, and a grouping of five numerical values representative of the disease state within a 6×1 rectangle.

14. The method of claim 12 wherein:
the motifs comprise distinct shapes.

15. The method of claim 11 further comprising:
filtering out the numerical values from the pattern that are below a limit prior to determining the statistical likelihood of the pattern of the numerical values occurring on the test plate.

16. The method of claim 11 further comprising:
when the statistical likelihood is less than the threshold value, transmitting an instruction from the quality assurance server to re-test the samples; and
applying the samples to a new test plate, wherein an arrangement of the samples on the new test plate is different from an arrangement of the samples on the test plate.

17. The method of claim 11 wherein:
the reagent selectively reacts with the portions of the genetic material that correspond with the disease state to generate fluorescence; and
determining the numerical value for each of the wells that quantifies the visual appearance of the well comprises determining the numerical value for each of the wells that quantifies a fluorescence intensity of the well.

18. The method of claim 11 further comprising:
adjusting the threshold value based on a volume of test plates being analyzed per unit time.

19. The method of claim 11 wherein:
the disease state is a Coronavirus Disease (COVID) disease state, the reagent comprises a fluorescent reporter molecule, and the numerical values indicate fluorescence intensities, and
the method further comprises comparing the numerical values to distinct ranges of fluorescence intensities that each correspond with a different diagnostic result relating to COVID.

20. A non-transitory computer readable medium embodying programmed instructions which, when executed by a processor, are operable for performing a method for controlling quality by identifying potential contamination at test plates, the method comprising:
applying samples of genetic material to a test plate comprising an array of wells;
performing Polymerase Chain Reaction (PCR) to amplify the genetic material at the array of wells for reaction with a reagent at the wells, wherein the reagent selectively reacts with portions of the genetic material that correspond with a disease state;
determining, at an analysis device, a numerical value for each well of the wells based on a change in a visual appearance caused by the amplification of the genetic material at the well, wherein the numerical value indicates whether a corresponding sample at the well is representative of the disease state;
receiving, at a quality assurance server, numerical values for the wells and location information indicating a location of each of the wells on the test plate;
identifying, at the quality assurance server, a pattern of the numerical values based on the location information, wherein the pattern comprises an arrangement of the numerical values of the array of wells at the test plate;
determining, at the quality assurance server, a statistical likelihood of the pattern of the numerical values assuming a random distribution of the numerical values; and
when the statistical likelihood is less than a threshold value,
determining, at the quality assurance server, that the arrangement of the numerical values of the array of wells at the test plate is statistically improbable and indicative of a potential contamination of liquid spilling between adjacent ones of the wells; and
flagging the test plate as potentially contaminated.

* * * * *